(12) United States Patent
Gin et al.

(10) Patent No.: US 7,931,824 B2
(45) Date of Patent: Apr. 26, 2011

(54) SURFACTANTS AND POLYMERIZABLE SURFACTANTS BASED ON ROOM-TEMPERATURE IONIC LIQUIDS THAT FORM LYOTROPIC LIQUID CRYSTAL PHASES WITH WATER AND ROOM-TEMPERATURE IONIC LIQUIDS

(75) Inventors: Douglas L. Gin, Longmont, CO (US); Jason E. Bara, Boulder, CO (US); Richard D. Noble, Boulder, CO (US); Xiaohui Zeng, Dublin, OH (US)

(73) Assignee: The Regents of The University of Colorado, Denver, CO (US)

( * ) Notice: Subject to any disclaimer, the term of this patent is extended or adjusted under 35 U.S.C. 154(b) by 192 days.

(21) Appl. No.: 11/773,044

(22) Filed: Jul. 3, 2007

(65) Prior Publication Data
US 2008/0029735 A1 Feb. 7, 2008

Related U.S. Application Data

(60) Provisional application No. 60/806,524, filed on Jul. 3, 2006.

(51) Int. Cl.
*C09K 19/38* (2006.01)
*C09K 19/52* (2006.01)
*C09K 19/54* (2006.01)
*C07D 403/06* (2006.01)
*C07D 403/12* (2006.01)

(52) U.S. Cl. ............. 252/299.01; 252/299.5; 548/312.7; 548/313.7; 548/341.1; 548/341.5

(58) Field of Classification Search ............. 252/299.01, 252/299.5; 548/313.7, 314.4, 341.1, 341.5, 548/312.7; 524/106
See application file for complete search history.

(56) References Cited

U.S. PATENT DOCUMENTS

| 3,853,907 | A | | 12/1974 | Edwards |
| 3,911,133 | A | | 10/1975 | Edwards |
| 4,024,146 | A | * | 5/1977 | Habermeier et al. ......... 544/314 |
| 5,631,274 | A | | 5/1997 | Austin et al. |
| 5,643,498 | A | * | 7/1997 | Li et al. .......................... 516/199 |
| 5,849,215 | A | | 12/1998 | Gin et al. |
| 6,358,914 | B1 | | 3/2002 | Gabriel et al. |
| 6,727,023 | B2 | | 4/2004 | Ono |

(Continued)

FOREIGN PATENT DOCUMENTS

JP 2002020428 1/2002

(Continued)

OTHER PUBLICATIONS

Anderson et al. (Web Release Dec. 23, 2004) "Structure and Properties of High Stability Geminal Dicationic Ionic Liquids," *J. Am. Chem. Soc.* 127(2):593-604.

(Continued)

*Primary Examiner* — Shean C Wu
(74) *Attorney, Agent, or Firm* — Greenlee Sullivan P.C.

(57) ABSTRACT

A modular surfactant architecture based on room temperature ionic liquids (RTILs) has been developed that affords non-polymerizable and polymerizable amphiphiles that form lamellar (L), hexagonal (H) or bicontinuous cubic (Q) LLC phases when mixed with water or RTILs serving as the polar solvent. The amphiphiles are imidazolium salts having two or more imidazolium head groups joined by one or more spacers. Polymerization of the LLC assembly can produce polymeric materials having ordered nanopores, with the ordering of the pores determined by the LLC phase.

24 Claims, 11 Drawing Sheets

U.S. PATENT DOCUMENTS

| | | | |
|---|---|---|---|
| 6,750,352 B2* | 6/2004 | Ono et al. | 548/341.5 |
| 7,090,788 B2* | 8/2006 | Elliott | 252/299.01 |
| 7,153,973 B2* | 12/2006 | Lazzari et al. | 548/300.7 |
| 7,521,003 B2 | 4/2009 | Gin et al. | |
| 2006/0025598 A1 | 2/2006 | Armstrong et al. | |
| 2006/0096922 A1* | 5/2006 | Gin et al. | 210/650 |
| 2007/0293684 A1* | 12/2007 | Fudemoto et al. | 548/335.1 |
| 2008/0296305 A1* | 12/2008 | Wyse et al. | 220/565 |
| 2008/0319202 A1 | 12/2008 | Gin et al. | |
| 2009/0173693 A1 | 7/2009 | Gin et al. | |

FOREIGN PATENT DOCUMENTS

| | | |
|---|---|---|
| WO | WO 2006/053083 | 5/2006 |
| WO | WO 2010/111308 | 9/2010 |

OTHER PUBLICATIONS

Bara et al. (Web Release Sep. 7, 2007) "Synthesis and Light Gas Separations in Cross-Linked Gemini Room Temperature Ionic Liquid Polymer Membranes," *J. Membr. Sci.* 316:186-191.

Bara et al. (Aug. 1, 2008) "Improving $CO_2$ selectivity in polymerized room-temperature ionic liquid gas separation membranes through incorporation of polar substituents," *J. Membr. Sci.* 321(1):3-7.

Bara et al. (Web Release Nov. 21, 2008) "Effect of Anion on Gas Separation Performance of Polymer-Room-Temperature Ionic Liquid Composite Membranes," *Ind. Eng. Chem. Res.* 47(24):9919-9924.

Bara et al. (Web Release Jul. 25, 2008) "Improving $CO_2$ permeability in polymerized room-temperature ionic liquid gas separation membranes through the formation of a solid composite with a room-temperature ionic liquid" *Polym. Adv. Technol.* 19(10):1415-1420.

Bara et al. (Web Release Jul. 6, 2007) "Enhanced $CO_2$ Separation Selectivity in Oligo(ethylene glycol) Functionalized Room-Temperature Ionic Liquids", *Ind. Eng. Chem. Res.* 46(16):5380-5386.

Binnemans, K. (Web. Release Nov. 9, 2005) "Ionic Liquid Crystals," *Chem. Rev.* 105(11):4148-4204.

Blasig et al. (Web Release Jul. 17, 2007) "Carbon Dioxide Solubility in Polymerized Ionic Liquids Containing Ammonium and Imidazolium Cations from Magnetic Suspension Balance: P[VBTMA][$BF_4$] and P[VBMI][$BF_4$] ." *Ind. Eng. Chem. Res.* 46(17):5542-5547.

Bradley et al. (Web Release Jan. 16, 2002) "Small-Angle X-Ray Scattering Studies of Liquid Crystalline 1-Alkyl-3-methylimidazolium Salts," *Chem. Mater.* 14(2):629-635.

Carlin et al. (1997) "Ionic Liquid-Polymer Gel Catalytic Membrane," *Chem. Commun.* 15:1345-1346.

Dreja et al. (1998) "Cationic Amphitropic Gemini Surfactants with Hydrophilic oligo(oxyethylene) Spacer Chains," *Chem. Commun.* 13:1371-1372.

Firestone et al. (Web Release Jul. 29, 2004) "Anion Effects on Ionogel Formation in *N,N'*-dialkylimidazolium-Based Ionic Liquids," *Inorg. Chim. Acta* 357:3991-3998.

Firestone et al. (Web Release Aug. 30, 2002) "Lyotropic Liquid-Crystalline Gel Formation in a Room-Temperature Ionic Liquid," *Langmuir* 18(2):7258-7260.

Gin et al. (Mar. 2006) "Recent Advances in the Design of Polymerizable Lyotropic Liquid-Crystal Assemblies for Heterogeneous Catalysis and Selective Separations," *Adv. Funct. Mater.* 16(7):865-878.

Gin et al. (Web Release Oct. 26, 2001) "Polymerized Lyotropic Liquid Crystal Assemblies for Materials Applications," *Acc. Chem. Res.* 34(12):973-980.

Han et al. (Web Release Aug. 23, 2005) "Using Geminal Dicationic Ionic Liquids as Solvents for High-Temperature Organic Reactions," *Org. Lett.* 7(19):4205-4208.

Holbrey et al. (1999) "The Phase Behavior of 1-alkyl-3-methylimidazolium Tettrafluoroborates; Ionic Liquids and Ionic Liquid Crystals," *J. Chem. Soc. Dalton Trans. Inorg. Chem.* 13:2133-2139.

Hu et al. (Web Release Mar. 28, 2006) "CO2 Permeability, Diffusivity and Solubility in Polyethylene Glycol-Grafted Polyionic Membranes and Their $CO_2$ Selectivity Relative to Methane and Nitrogen," *J. Membr. Sci.* 281:130-138.

Ichikawa et al. (Sep. 5, 2007) "Self-Organization of Room-Temperature Ionic Liquids Exhibiting Liquid-Crystalline Bicontinuous Cubic Phases: Formation of Nano-Ion Channel Networks," *J. Am. Chem. Soc.* 129(35):10662-10663.

Inoue et al. (Mar. 15, 2007) "Phase Behavior of Binary Mixture of 1-dodecyl-3-methylimidazolium Bromide and Water Revealed by Differential Scanning Calorimetry and Polarized Optical Microscopy," *J. Colloid Interface Sci.* 307(2):578-581.

Jin et al. (Web Release Feb. 6, 2006) "Polyethylene Glycol Functionalized Dicationic Ionic Liquids with Alkyl or Polyfluoroalkyl Substituents as High Temperature Lubricants," *J. Mater. Chem.* 16:1529-1535.

Lee et al. (2000) "Simple Amphiphilic Liquid Crystalline *N*-Alkylimidazolium Salts. A New Solvent System Providing a Partially Ordered Environment," *Chem. Commun.* 19:1911-1912.

Lee et al. (May 1995) "Polymerization of Nonlamellar Lipid Assemblies," *J. Am. Chem. Soc.* 117(20):5573-5578.

Lu et al. (Dec. 2006) "Crosslinked Bicontinuous Cubic Lyotropic Liquid-Crystal/Butyl-Rubber Composites: Highly Selective, Breathable Barrier Materials for Chemical Agent Protection," *Adv. Mater.* 18(24):3296-3298.

Menger et al. (Jun. 2, 2000) "Gemini Surfactants," *Angew. Chem. Int. Ed.* 39(11):1906-1920.

Mukai et al. (Web Release Jan. 20, 2005) "Anisotropic Ion Conduction in a Unique Smectic Phase of Self-Assembled Amphiphilic Ionic Liquids," *Chem. Commun.* 10:1333-1335.

Mukai et al. (2004) "Effect of Methyl Groups onto Imidazolium Cation Rings on Liquid Crystallinity and Ionic Conductivity of Amphiphilic Ionic Liquids," *Chem. Lett.* 33(12):1630-1631.

Nakajima et al. (Web Release Oct. 20, 2005) "Preparation of Thermally Stable Polymer Electrolytes from Imidazolium-Type Ionic Liquid Derivatives," *Polymer* 46:11499-11504.

Ohno et al. (Nov. 30, 2004) "Development of a New Class of Ion Conductive Polymers Based on Ionic Liquids," *Electrochim. Acta* 50(2-3):255-261.

Paleos, C.M. (1992) "Polymerization of Micelle-Forming Monomers," In; *Polymerizations in Organized Media*, Gordon and Breach, Philadelphia, pp. 183-214.

Pindzola (Feb. 12, 2003) "Cross Linked Normal Hexagonal and Bicontinuous Cubic Assemblies via Polymerizable Gemini Amphiphiles," *J. Am. Chem. Soc.* 125(10):2940-2949.

Sneddon et al. (May 15, 2003) "Cross-Linked Polymer-Ionic Liquid Composite materials," *Macromolecules* 36(12):4549-4556.

Srisiri et al. (Mar. 12, 1998) "Stabilization of a Bicontinuous Cubic Phase from Polymerizable Monoacylglycerol and Diacylglyerol," *Langmuir* 14(7):1921-1926.

Tang et al. (Web Release May 27, 2005) "Poly(ionic liquid)s: a new material with enhanced and fast $CO_2$ Absorption," *Chem. Commun.* 26:3325-3326.

Tang et al. (Web Release Feb. 18, 2005) "Enhanced $CO_2$ Absorption of Poly(ionic liquid)s," *Macromolecules* 38(6):2037-2039.

Tiddy, G.J.T. (Jan. 1980) "Surfactant-Water Liquid Crystal Phases," *Phys. Rep.* 57(1):1-46.

Wang et al. (Web Release Apr. 12, 2005) "Hexagonal Liquid Crystalline Phases Formed in Ternary Systems of Brij 97-Water-Ionic Liquids," *Langmuir* 21(11):4931-4937.

Wang et al. (2004) "Lyotropic Liquid Crystalline Phases Formed in an Ionic Liquid," *Chem. Commun.* 24:2840-2841.

Washiro et al. (2004) "Highly Ion Conductive Flexible Films Composed of Network Polymers Based on Polymerizable Ionic Liquids," *Polymer* 45:1577-1582.

Yan et al. (Web Release May 22, 2006) "Surfactant Ionic Liquid-Based Microemulsions for Polymerization" *Chem. Commun.* 25:2696-2698.

Yang et al. (2002), "Polymerized Bicontinuous Cubic Nanoparticles (Cubosomes) from a Reactive Monoacylglycerol," *J. Am. Chem. Soc.* 124(45):13388-13389.

Yoshio et al. (2004) "Self-Assembly of an Ionic Liquid and a Hydroxyl-Terminated Liquid Crystal: Anisotrpoic Ion Conduction in Layered Nanostructures," *Mol. Cryst. Liq. Cryst.* 413:2235-2244.

Yoshio et al. (2002) "Liquid-Crystalline Assemblies Containing Ionic Liquids: An Approach to Anisotropic Ionic Materials," *Chem. Lett.* 320-321.

Yoshio et al. (2004) "One-Dimensional Ion Transport in Self-Organized Columnar Ionic Liquids," *J. Am. Chem. Soc.* 126(4):994-995.

Yoshio et al. (Web Release Mar. 31, 2006) "One-Dimensional Ion-Conductive Polymer Films: Alignment and Fixation of Ionic Channels Formed by Self-Organization of Polymerizable Columnar Liquid Crystals," *J. Am. Chem. Soc.* 128(16):5570-5577.

Yoshio et al. (Mar. 4, 2002) "Layered Ionic Liquids: Anisotropic Ion Conduction n New Self-Organized Liquid-Crystalline Materials," *Adv. Mater.* 14(5):351-354.

J. Bara (Sep. 2007) "New ionic liquids and ionic liquid-based polymers and liquid crystals for gas separations," Ph.D. Thesis, University of Colorado at Boulder, Introductory Material and Chapters 1, and 5-6, pp. i-xvii, 1-26, 90-152.

J. Bara (Feb. 12, 2007), private communication, "Compositions of Matter for Joint Patent Application", 9 pages.

* cited by examiner

R = –(CH$_2$)$_x$–  
= –(OCH$_2$)$_y$–

X$^-$ = Br$^-$  
= BF$_4^-$ m = 0 to 6

PG = polymerizable group (e.g.,

)

SURFACTANTS AND POLYMERIZABLE SURFACTANTS BASED ON ROOM-TEMPERATURE IONIC LIQUIDS THAT FORM LYOTROPIC LIQUID CRYSTAL PHASES WITH WATER AND ROOM-TEMPERATURE IONIC LIQUIDS

CROSS-REFERENCE TO RELATED APPLICATIONS

This application claims the benefit of U.S. Provisional Application No. 60/806,524, filed Jul. 3, 2006, which is hereby incorporated by reference to the extent not inconsistent with the disclosure herein.

ACKNOWLEDGEMENT OF GOVERNMENT SUPPORT

This invention was made at least in part with support from the United States Government under National Science Foundation Grant No. DMR-0111193. The United States Government has certain rights in this invention.

BACKGROUND OF THE INVENTION

This invention is in the field of lyotropic liquid crystal (LLC) materials, in particular, cationic imidazolium surfactants that can form LLC phases when mixed with water or room temperature ionic liquids (RTILS) as the solvent. The imidazolium surfactants may be polymerizable.

Lyotropic liquid crystals (LLCs) are amphiphilic molecules (i.e., surfactants) containing one or more hydrophobic organic tails and a hydrophilic headgroup, that spontaneously organize in the presence of water or another polar solvent to form highly ordered yet fluid, phase-separated assemblies with periodic polar and non-polar domains on the 1-10 nm scale (FIG. 1) (Tiddy, G. J. T. *Phys. Rep.* 1980, 57, 1-46; Seddon, J. M. *Biochim. Biophys. Acta* 1990, 1031, 1). LLC phases include the normal hexagonal ($H_I$) phase, the lamellar (L) phase, bicontinuous cubic (Q) phases, and the inverted hexagonal ($H_{II}$) phase. FIG. 1 illustrates these phases for LLC mesogens with hydrophilic headgroups and hydrophobic organic tails in water or other polar solvent. As shown in FIG. 1, the $H_I$ phase has rod-like micelles arranged in a hexagonal array. The surface of the rod-like micelles is composed of the hydrophilic head groups of the LLCs, while the hydrophobic tails are isolated inside the micellar rods. The L (planar bilayer) phase in FIG. 1 has a double layer of molecules arranged so that the headgroups form the surface of the layer while the hydrophobic tails are isolated inside the layer. In the $H_{II}$ phase shown in FIG. 1, water-filled cylindrical channels are arranged in a hexagonal array. The hydrophilic headgroups surround the channels of water while the hydrophobic tails fill the volume between the channels of water. In the Q phases, channels or interconnected manifolds of water or other polar solvent are connected as a three-dimensional network surrounded by an organic bilayer of the LLCs. The hydrophilic headgroups of the amphiphiles surround the channels of polar solvent, or vice versa. These phases are termed bicontinuous because they have two or more unconnected but interpenetrating hydrophobic and/or aqueous or polar solvent networks with overall cubic symmetry. Depending on where they appear on the phase diagram relative to the central lamellar (Lα) phase, these Q phases can be classified as Type I (oil-in-water or normal) or Type II (water-in-oil or inverted). FIG. 2 illustrates two $Q_I$ phases and two $Q_{II}$ phases (both Ia3d and Pn3m) in which the interpenetrating organic networks (dark) are separated from one another by a continuous water layer surface (light) with overall cubic symmetry When these LLC phases are successfully cross-linked, robust polymer materials with unique nanoporous architectures are generated (Mueller, A.; O'Brien, D. F. *Chem. Rev.* 2002, 102, 727; Miller, S. A.; Ding, J. H.; Gin, D. L. *Curr. Opin. Colloid Interface Sci.* 1999, 4, 338; O'Brien, D. F.; Armitage, B.; Benedicto, A.; Bennet, D. E.; Lamparski, H. G.; Lee, Y.-K.; Srisiri, W.; Sisson, T. M. *Acc. Chem. Res.* 1998, 31, 861-868), These nanoporous LLC polymer networks have been shown to be highly valuable as heterogeneous catalysts, molecular size-selective filtration membranes, and selective vapor barrier materials when water is used to form the LLC phases and in the hydrophilic channels (Gin, D. L.; Lu, X.; Nemade, P. R.; Pecinovsky, C. S.; Xu, Y.; Zhou, M. *Adv. Funct. Mater.* 2006, 16, 865878; Gin, D. L.; Gu, W.; Pindzola, B. A.; Zhou, W.-J. *Acc. Chem. Res.* 2001, 34, 973-980) Enhanced performance such as improved reactivity, selectivity, and/or transport of molecules can arise when reactions or transport occur in either the ordered nanostructured aqueous or hydrocarbon domains.

Recently, there has been a great deal of academic and industrial interest in room-temperature ionic liquid (RTILs), as well as in new polymer- and liquid crystal (LC)-based materials containing RTILs. RTILs are organic salts that are liquid at or below 100° C., and are composed entirely of cations and anions (i.e., free of any additional solvents) (Welton, T. Chem. Rev. 1999, 99, 2071-2083; Welton, T. *Coord. Chem. Rev.* 2004, 248, 2459-2477). They have attracted broad interest as novel solvents and liquid media for a number of applications because they have a unique combination of liquid properties. They have very low volatility, relatively low viscosity, high thermal stability, low flammability, high ionic conductivity, tunable polar salvation and transport properties, and in some cases, even catalytic properties. These characteristics have made RTILs excellent candidates as environmentally benign solvents to replace conventional organic solvents in many chemical, electrochemical, and physical extraction/separation processes In addition, RTILs have been shown to be novel gas separation media in supported liquid membranes (SLMs), (Scovazzo, P.; Visser, A. E.; Davis, J. H., Jr.; Rogers, R. D.; Koval, C. A.; DuBois, D. L.; Noble, R. D. "Supported Ionic Liquid Membranes and Facilitated Ionic Liquid Membranes," ACS Symposium Series 818 (Ionic Liquids), 2002, 69-87; Schaefer, T.; Branco, L. C.; Fortunato, R.; Izak, P.; Rodrigues, C. M.; Afonso, C. A. M.; Crespo, J. G. "Opportunities for Membrane Separation Processes using Ionic Liquids," ACS Symposium Series 902 (Ionic Liquids IIIB: Fundamentals, Progress, Challenges, and Opportunities), 2005, 97-110) and novel catalysts in a number of chemical processes (Welton, 1999, 2000), with performance enhancements in both cases due to the unique properties of RTILs.

One area of specific interest within the area of RTILs is the development of nanostructured polymer- and/or LC-derived RTIL materials. A collective goal of this latter work is the design of solid, immobilized RTIL materials and anisotropic gels with most of the desirable characteristics of RTILs, but without the mechanical limitations of a liquid (Ohno, H.; Yoshizawa, M.; Ogihara, W. *Electrochim. Acta* 2004, 50, 255-261). Most of the work in this latter area has centered around polymerizable RTILs (Washiro, S.; Yoshizawa, M.; Nakajima, H.; Ohno, H. *Polymer* 2004, 45, 1577-1582; Ohno, H.; Yoshizawa, M.; Ogihara, W. *Electrochim. Acta* 2004, 50, 255-261; Nakajima, H.; Ohno, H. *Polymer* 2005, 46, 11499-11504); RTIL-polymer composites (Carlin, R. T.; Fuller, *J. Chem. Commun.* 1997, 1345; Sneddon, P.; Cooper, A. I.;

Scott, K.; Winterton, N.; *Macromolecules* 2003, 36, 4549-4556); surfactant LC-RTIL blends (Wang, L.; Chen, X.; Chai, Y.; Hao, J.; Sui, Z.; Zhuang, W.; Sun, Z. *Chem. Commun.* 2004, 2840-2841; Wang, Z.; Liu, F.; Gao, Y.; Zhuang, W.; Xu, L.; Han, B.; Li, G.; Zhang, G. *Langmuir* 2005, 21, 4931-4937); RTIL-derived LC systems (Bradley, A. E.; Hardacre, C.; Holbrey, J. D.; Johnston, S.; McMath, S. E. J.; Nieuwenhuyzen, M. *Chem. Mater.* 2002, 14, 629-635; Yoshio, M.; Mukai, T.; Kanie, K.; Yoshizawa, M.; Ohno, H.; Kato, T. *Chem. Lett.* 2002, 320-321; Firestone, M. A.; Dzielawa, J. A.; Zapol, P.; Curtiss, L. A.; Seifert, S.; Dietz, M. L. *Langmuir* 2002, 18, 7258-7260; Firestone, M. A.; Rickert, P. G.; Seifert, S.; Dietz, M. L. *Inorg. Chim. Acta* 2004, 357, 3991-3998; Yoshio, M.; Mukai, Ohno, H.; Kato, T. J. *Am. Chem. Soc.* 2004, 126, 994-995; Mukai, T.; Yoshio, M.; Kato, T.; Yoshizawa, M.; Ohno, H. *Chem. Commun.* 2005, 1333-1335; Binnemans, K. *Chem. Rev.* 2005, 105, 4148-4204); and most recently, polymerizable RTIL-based LC systems (Yoshio, M.; Kagata, T.; Hoshino, K.; Mukai, T.; Ohno, H.; Kato, T. *J. Am. Chem. Soc.* 2006, 128, 5570-5577). Most of these endeavors have been directed towards designing better solid-state ion conductors and anisotropic ion conductors for batteries and energy storage.

Prior RTIL-LC and RTIL-derived LC materials have been reported with 1-D columnar hexagonal and 2-D lamellar LC and LLC morphologies (Wang 2004; Wang 2005; Bradley 2002; Yoshio 2002; Firestone 2002, Firestone 2004; Yoshio 2004; Mukai 2005; Binnemans; 2005; Yoshio 2006). There is also a report of an RTIL-derived single-head/single-tail surfactant that formed a transient LLC phase with Q like character when mixed with water. However, the authors state in their paper that this LLC phase lacks the XRD peaks to support a Q phase and that it is better described as a hexagonal type phase with some cubic character (Firestone 2004).

A few examples of RTILs and polymerizable RTILs with two joined (i.e., gemini) imidazolium headgroups has been reported in the literature These systems include isotropic liquids for applications such as solvents and high-temperature lubricants (Anderson, J. L.; Ding, R.; Ellern, A.; Armstrong, D. W. *J. Am. Chem. Soc.* 2005, 127, 593-604; Jin, C.-M.; Ye, C.; Phillips, B. S.; Zabinski, J. S.; Liu, X.; Liu, W.; Schreeve, J. M. *J. Mater. Chem.* 2006, 16, 1529-1535); or precursors to non-ordered polymers (Nakajima, H.; Ohno, H. *Polymer* 2005, 46, 11499-11504).

Also, antibacterial bis(imidazolium quaternary salts) have been reported U.S. Pat. No. 3,853,907 to Edwards et al.

One of the most sought-after goals in the area of nanostructured RTIL-LC or polymer materials is the design and synthesis of Q-phase composites containing RTIL components, especially for ion conducting materials. Unfortunately, only a handful of polymerizable small molecule surfactants are known in the prior art that can be polymerized in Q phases (for examples, see Lee, Y.-S.; Yang, J.-Z.; Sisson, T. M.; Frankel, D. A.; Gleeson, J. T.; Aksay, E.; Keller, S. L.; Gruner, S. M.; O'Brien, D. F. *J. Am. Chem. Soc.* 1995, 117, 5573; Srisiri, W.; Benedicto, A.; O'Brien, D. F.; Trouard, T. P. *Langmuir* 1998, 14, 1921; Yang, D.; O'Brien, D. F.; Marder, S. R. *J. Am. Chem. Soc.* 2002, 124, 13388; Pindzola, B. A.; Jin, J.; Gin, D. L. *J. Am. Chem. Soc.* 2003, 125, 2940-2949). These exemplary Q-phase LLC monomer systems were designed to interface with and form Q-phases around water as the polar solvent, not RTILs.

Consequently, there remains a need for new surfactants and polymerizable surfactants that can form LLC phases with RTILs and other polar solvents to generate superior nanocomposite materials for enhanced application performance.

BRIEF SUMMARY OF THE INVENTION

The current invention provides surfactant molecules that interface with and form nanostructured LLC assemblies with RTILs or water. A modular surfactant architecture based on RTILs has been developed that affords non-polymerizable and polymerizable amphiphiles that form lamellar (L), hexagonal (H) or bicontinuous cubic (Q) LLC phases when mixed with water or RTILs serving as the polar solvent. The phase formed depends on the surfactant structure, and the composition, temperature, and pressure of the system.

In an embodiment, the RTIL-based surfactants and polymerizable surfactants of the invention have the unique ability to form special Q-type LLC phases containing ordered 3-D, interconnected nanopores with water or RTILs encapsulated by the hydrophilic nanodomains. Such monomers and behavior are believed to be unprecedented in the LLC and RTIL-LC areas. The high pore accessibility and molecular-size selectivity of the bicontinuous cubic structure combined with the unique chemical properties of the RTILs in the channels are believed to be unprecedented and may enhance performance in the areas of nanofiltration, gas separations, vapor barrier materials, ion conduction, protein anti-fouling, electrochemistry, and catalysis.

The polymerizable versions of these surfactants can be made into permanent nanoporous organic materials via in situ polymerization. Cross-linked Q LLC assemblies hold great promise as nanoporous organic catalyst supports and membrane materials because of their interconnected, nanometer-scale solvent domains. Their unique 3-D interconnected solvent pore morphologies (at least 3 different cubic architectures) (Fontell, K. "*Colloid Polym. Sci.* 1990, 268, 264; Tate, M. W.; Eikenberry, E. F.; Turner, D. C.; Shyamsunder, E.; Gruner, S. M. *Chem. Phys. Lipids* 1991, 57, 147) (FIG. 2) provide better pore access and transport continuity than the 1-D $H_{II}$ and 2-D L phases. In addition, they do not require alignment for optimal transport, nor do they sacrifice the molecule-size selectivity properties that come with having well-defined nanopores.

The surfactants and polymerizable surfactants of the invention are gemini (i.e., two-headed) amphiphiles consisting of two joined cationic imidazolium groups substituted with long hydrophobic tails to give the resulting molecules amphiphilic behavior. The gemini imidazolium headgroup motif is very modular in construction, thereby allowing simple yet broad control over surfactant structure, shape, and introduction of additional chemical groups, which is uncommon in gemini surfactant and LLC design (Menger, F. M.; Keiper, J. S. *Angew. Chem. Int. Ed.* 2000, 39, 1906). The imidazolium headgroups on these compounds are ionic, hydrophilic, and also similar to imidazolium-based RTIL molecules, thereby allowing good interfacial compatibility and LLC phase formation with water as well as RTILs as solvents.

In an embodiment, the surfactant composition has the general formula:

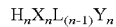  Formula 1 where n is greater than or equal to 2; H is a hydrophilic head group comprising a five membered aromatic ring containing two nitrogens (e.g. an imidazolium ring); X is an anion, L is a spacer or linking group which connects two rings, and Y is a hydrophobic tail group attached to each ring and having at least 10 carbon atoms and optionally comprises a polymerizable group P. Each spacer L is attached to a first nitrogen atom in each of the two linked rings. The attachment may be through a covalent or a noncovalent bond such as an ionic linkage. Each hydrophobic tail group Y is attached to the second (other, nonbridged) nitrogen atom in each ring. The combination of the hydrophilic head group H, the linker L, and the hydrophobic tail Y form an imidazolium cation. Hydrophobic tails may also be attached to one or more carbon atoms of the ring.

In an embodiment, n=2 and the surfactant composition has the general formula:

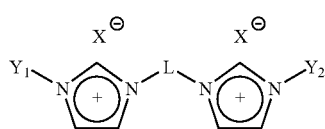

Formula 2

In another embodiment, n=2 and the surfactant composition has the general formula:

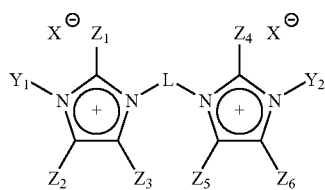

Formula 3

In Formula 3, $Z_1$ through $Z_6$ are individually selected from the group consisting of hydrogen and hydrophobic tail groups. In an embodiment, the hydrophobic tail group has between one and 12 carbon atoms and optionally comprises a polymerizable group P. Attachment of a hydrophobic tail to one or more carbon atoms in the ring in addition to the hydrophobic tail attached to the nitrogen can be used to tune LLC phase structure and curvature.

The invention also provides methods for synthesizing gemini surfactants and monomers. In an embodiment, the method for synthesizing the surfactants and monomers of the invention includes the steps of linking at least two imidazole rings and then forming an imidazolium salt, the salt having linked imidazolium rings and at least one hydrophobic tail attached to each imidazolium ring.

Compared to the syntheses of the handful of LLC monomers known to form Q phases in the literature (Lee 1995, Srisiri 1998, Yang 2002, Pindzola 2003), the synthesis methods of the invention are simpler, more modular, and allow a wider range of organic groups to be incorporated into the headgroups to make functional LLC derivatives. Using the synthesis schemes presented in FIGS. 4a and 4b, it is believed that other types of functional groups can be incorporated in the bridging linkage between the two imidazolium headgroups (e.g., catalytic groups, molecule receptors, etc.) by designing bridging units with the appended function group of interest. It is also believed that similar imidazolium-based non-polymerizable and polymerizable surfactants containing more than 2 joined headgroups (i.e., trimeric and higher surfactants) can be synthesized in a related manner.

The invention provides lyotropic liquid crystal systems which comprise the imidazolium-based surfactants or monomers of the invention and a polar solvent. In an embodiment, the invention provides a LLC system which forms the bicontinuous cubic structure, the LLC system comprising a surfactant composition of the invention and a solvent selected from the group consisting of water and room temperature ionic liquids and mixtures thereof. In an embodiment, the RTIL solvent is selected to have an anion matching that of the surfactant composition.

Control over the type of the LLC phase formed by the gemini surfactants and monomers of the invention can be achieved by systematically varying molecular parameters such as the type and length of the headgroup bridge linkage, the tails, and the anionic counterions. Substituents on the imidazolium headgroups can also be used to tune chemical and LLC phase formation properties. In addition, the type of LLC phase formed can also be controlled by varying external parameters, such as temperature, solvent concentration and type, and pressure (Tiddy 1980; Seddon 1990).

In addition, the non-ordered (i.e., amorphous or non-LLC) blends of the inventive imidazolium-derived surfactants and polymerizable surfactants with water and/or RTILs may also have interesting properties for ion conduction, gas separation, and electrochemical applications.

DETAILED DESCRIPTION

Figure 1:
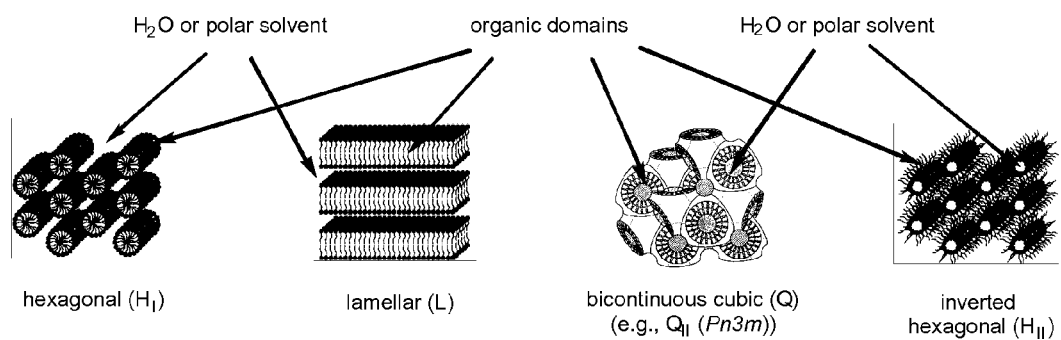
FIG. 1: Some common LLC phases formed by surfactants in the presence of water or other polar solvents.
Figure 2:
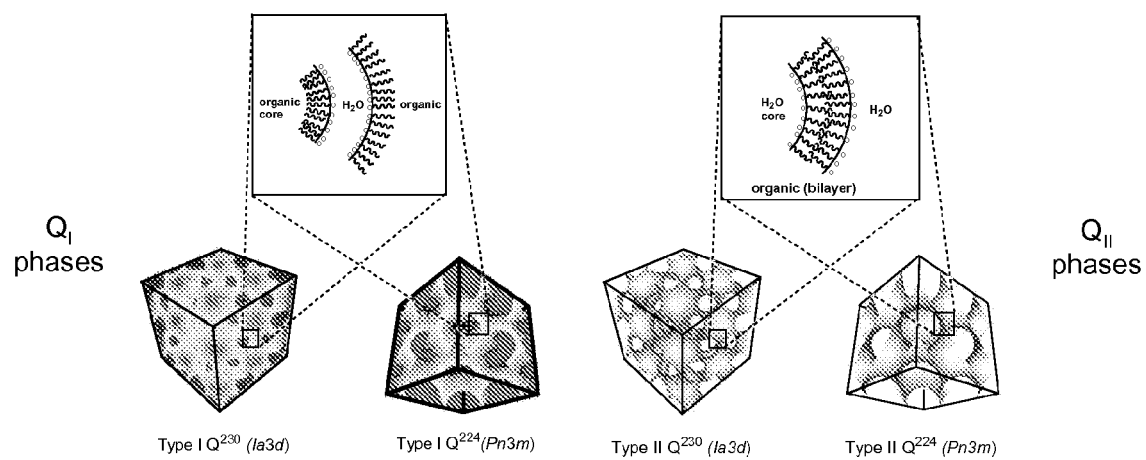
FIG. 2: Schematic representations of both type I and type II Q phases, showing the relative locations of the hydrocarbon (dark regions) and aqueous regions (light regions).

As used herein, LLC mesogens, amphiphiles or surfactants are amphiphilic molecules containing one or more hydrophobic organic tails and a hydrophilic headgroup that spontaneously self-assemble into fluid, yet highly ordered matrices with regular geometries of nanometer scale dimension when combined with water or another suitable polar organic solvent. The concentration of the amphiphile may be greater than that of the polar solvent. "LLC monomers" are polymerizable LLC mesogens.

Without wishing to be bound by any particular theory, it is believed that an extremely important factor in making LLC surfactants that will produce hexagonal or cubic phases is getting the aspect ratio or molecular shape right (truncated cone shape with the hydrophilic end the larger end) so that packing will prefer these phases. The molecular shape can be modified by changing the spacer length between the hydrophilic headgroups and the length of the hydrophobic tails on the gemini LLC. The molecular shape can also be modified by the number of hydrophobic tails attached to the headgroup, with multiple hydrophobic tails generally producing a more conical shape.

The phase adopted by the amphiphiles is also believed to depend upon the chemical composition and/or flexibility of the spacer group. For example, spacer groups incorporating hydrophilic groups (such as ethers) are believed to be less miscible with the hydrophobic tails than alkylene spacers, thereby encouraging segregation on the nanometer scale. Compatibility of ether groups with imidazolium cations in the amphiphile headgroups and in the RTIL solvent are also believed to promote organization at the headgroups in RTIL solvents.

The phase adopted by the amphiphile can also depend upon the nature of the polymerizable group attached to the hydrophobic tail. The polymerizable group may affect both the hydrophobicity of the tail and/or the packing of the amphiphiles. It is believed that LLC phase assembly of monomers with acrylate (including methacrylate) terminated tails can be more challenging than LLC phase assembly of monomers with diene terminated tails or surfactants with purely hydrocarbon tails for both these reasons.

The phase adopted by the amphiphile can also depend upon the nature of the solvent. Water will typically dissolve only in the hydrophilic headgroups. RTILs other than simple [emim][BF$_4$] may have a tendency to dissolve in other parts of the LCs.

The present invention provides LLC surfactant and monomer compositions. In an embodiment, the anion present in the surfactant or monomer, X, is a standard anion used in preparing room temperature ionic liquids. These anions include, but are not limited to, Br$^-$, BF$_4^-$, Cl$^-$, I$^-$, CF$_3$SO$_3^-$, Tf$_2$N$^-$ (and other large fluorinated anions), PF$_6^-$, DCA$^-$, MeSO$_3^-$, and TsO—. In an embodiment, the anion X is selected from the group consisting of Br$^-$ and BF$_4^-$ It is believed that amphiphile anions that are simple halogen ions (e.g. Br—) are generally suitable for use with aqueous solvents, but may not be as suitable for use with some RTILS.

In an embodiment, the spacer L can comprise an alkylene group, an ether group, an amide, an ester, an anhydride, a phenyl group, a perfluoro alkylene, a perfluoroether, or a siloxane. In an embodiment, L comprises an alkylene group having from 1 to about 12 carbons, or comprises from 1 to about 6 ether groups. In an embodiment, L comprises an alkylene group having from 4 to about 8 carbons. In an embodiment, L comprises 1 to 3 ether groups. In an embodiment, L can be described by the formula $(CH_2CH_2O)_p CH_2CH_2$ where p is from 1 to 3. In addition, the spacer L can include a pendant functional group such as a catalytic group or a molecule receptor, so long as the desired LLC phase is still obtained.

In an embodiment, Y is a hydrophobic tail group having at least 10 carbon atoms. In an embodiment, the hydrophobic tail groups Y attached to each headgroup of the molecule are the same. In an embodiment, Y has from 10 to 18 carbon atoms. The tail group may be linear or branched. A linking group may be placed between the tail and the ring. In an embodiment, Y comprises a linear alkyl chain of at least 10 carbon atoms. In another embodiment, Y comprises a polymerizable group P. In an embodiment, the polymerizable group terminates the tail. Y may comprise a linear alkylene chain attached to a polymerizable group P, with the tail as a whole having at least 10 carbon atoms. Suitable polymerizable groups include acrylate, methacrylate, diene, vinyl, (halovinyl), styrenes, vinylether, hydroxy groups, epoxy or other oxiranes (halooxirane), dienoyls, diacetylenes, styrenes, terminal olefins, isocyanides, acrylamides, and cinamoyl groups. In an embodiment, the polymerizable group is an acrylate, methacrylate or diene group. In another embodiment, the polymerizable group is an acrylate group. The tail group Y can have some portions that are more hydrophobic than others (e.g. if the tail group contains a polymerizable group attached to an alkylene chain), but the tail group is overall hydrophobic with respect to the headgroup portion of the molecule.

In Formula 3, $Z_1$ through $Z_6$ are individually selected from the group consisting of hydrogen and hydrophobic tail groups. In different embodiments, the hydrophobic tail group has from 1 to 18 carbons, 1 to 12 carbons or from 10 to 18 carbons. In an embodiment, Z is selected from the group consisting of hydrogen, methyl, ethyl, $C_{11}$, and $C_{17}$. In an embodiment, the two imidazolium rings have the same number of hydrophobic tail groups. In an embodiment, $Z_1$ and $Z_4$ are the same. In an embodiment, $Z_1$ and $Z_4$ are a hydrophobic tail group and $Z_2$, $Z_3$, $Z_5$ and $Z_6$ are hydrogen, so that an additional hydrophobic tail is attached to the carbon in between the two nitrogens in each ring. Any of $Z_1$-$Z_6$ may comprise a polymerizable group. Attachment of a hydrophobic tail to one or more carbon atoms in the ring in addition to the hydrophobic tail attached to the nitrogen can be used to tune LLC phase structure and curvature.

Figure 3:
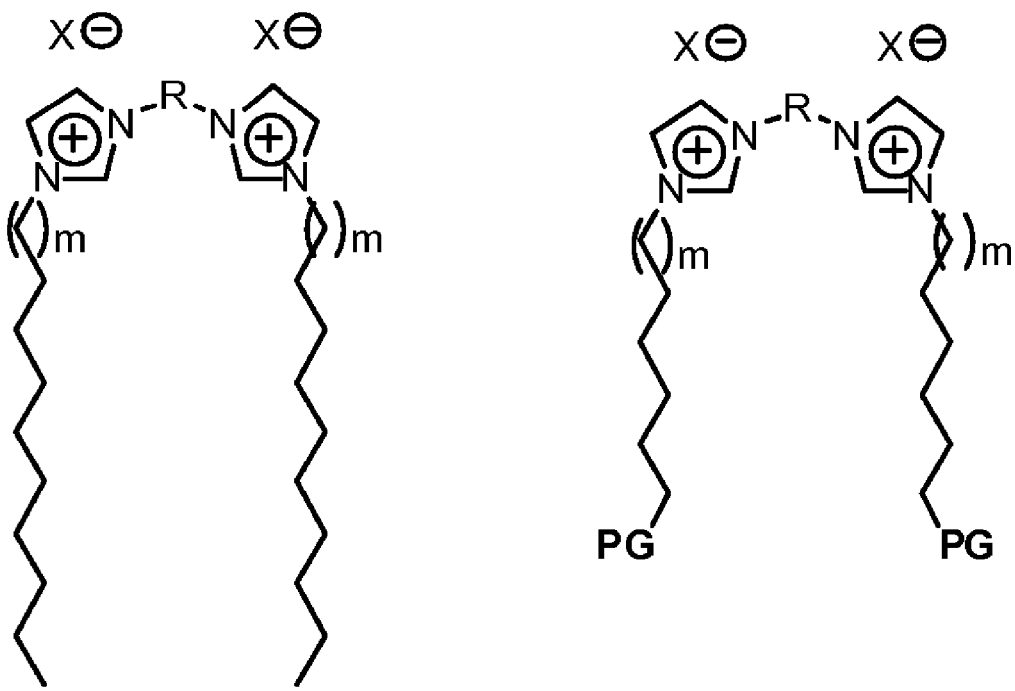
FIG. 3: Exemplary imidazolium-based gemini surfactants and polymerizable surfactants
Figure 3:
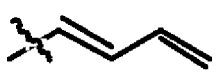
Figure 3:
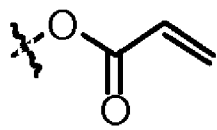

The surfactant compositions may also be described as shown in FIG. 3. In an embodiment, x is between 1 and 12 or y is between 1 and 6. In another embodiment, surfactants which form the bicontinuous cubic phase have R=(CH$_2$)$_x$, x=6, and X$^-$=BF4$^-$. Surfactants which form the bicontinuous cubic phase also can have R=(OCH$_2$)$_y$ and y=1 or 2.

Figure 4A:
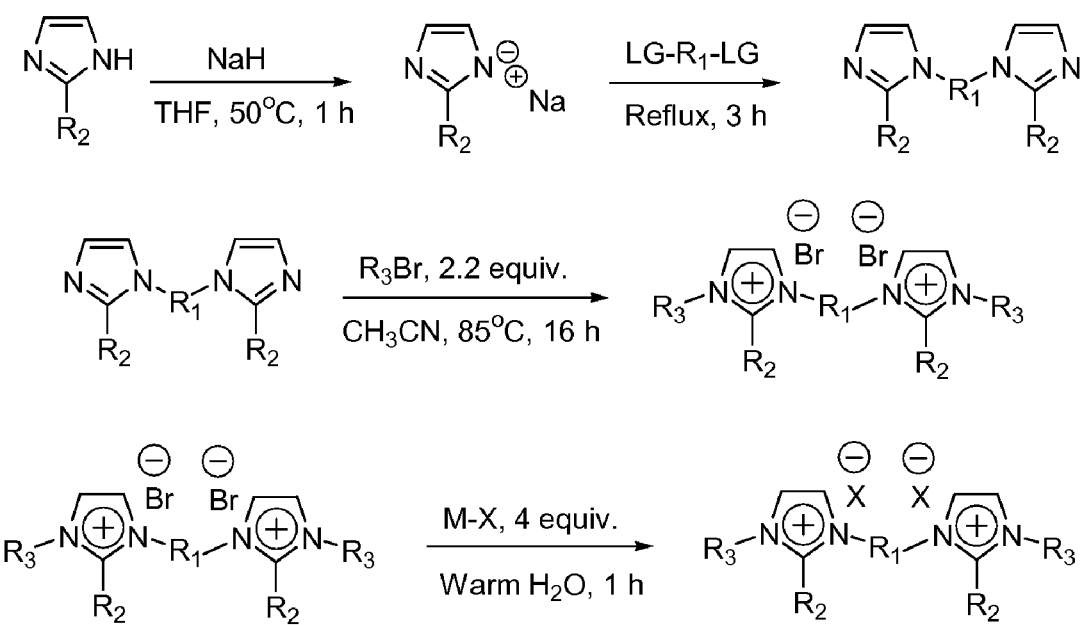
FIGS. 4a and 4b: Synthesis schemes for nonpolymerizable and polymerizable Gemini imidazolium-based surfactants.
Figure 4B:
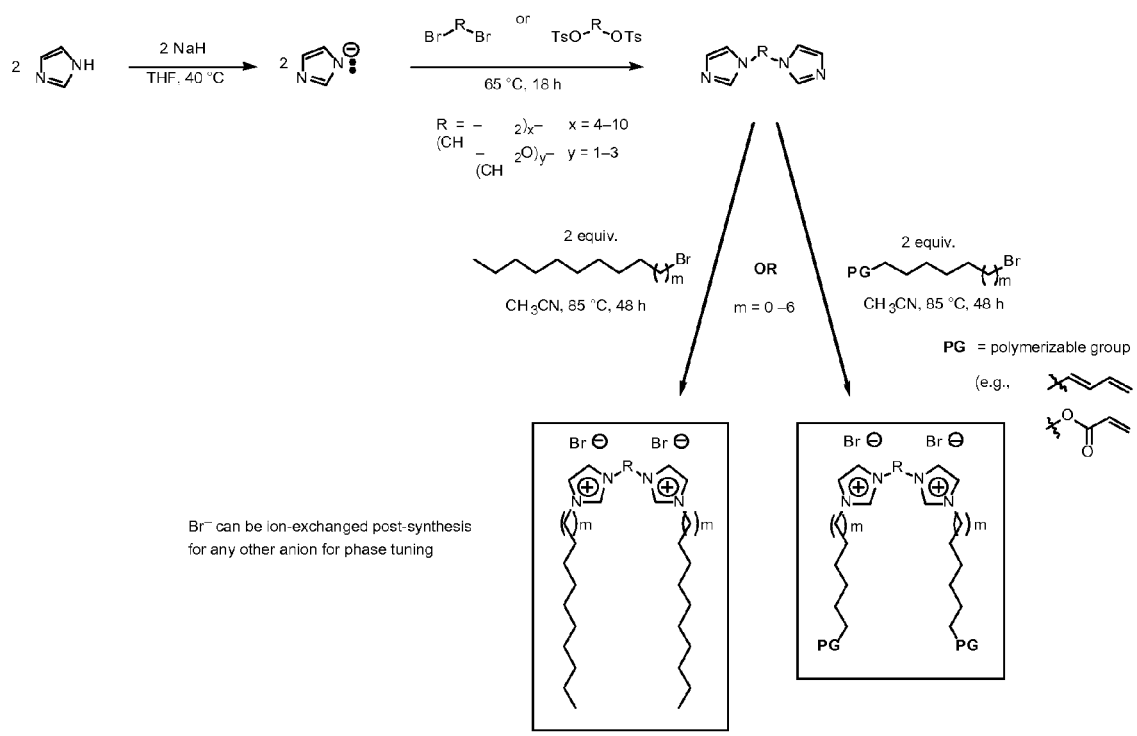

The Gemini amphiphiles of the invention can be made via a process in which two imidazole rings are joined with the spacer group, followed by attachment of a hydrophobic tail to the non-bridged nitrogen of the ring and generation of a halide imidazolium salt. Ion exchange can be used to make imidazolium salts having anions other than the halide salt. FIGS. 4$a$ and 4$b$ illustrate specific examples. In FIG. 4$a$, $Z_1$ and $Z_4$ of Formula 3 are R$_2$ and $Z_2$, $Z_3$, $Z_5$, and $Z_6$ are hydrogen. The spacer group L is denoted as R$_1$. FIG. 4$a$ also shows Y$_1$ and Y$_2$ as R$_3$. In FIG. 4$b$, $Z_1$-$Z_3$ and $Z_4$-$Z_6$ of Formula 3 are all hydrogen, the spacer group L is denoted by R, and Y$_1$ and Y$_2$ are shown as straight chain alkyl groups or straight chain alkylene groups attached to a polymerizable group PG.

The availability of various imidazole derivatives presents opportunities to modify the molecule structure. For example, the use of the commercially available 1-undecylimidazole in the first step of the synthesis can add extra hydrocarbon bulk at the carbon between the two nitrogen atoms in the ring (see FIG. 4$a$).

The hydrophobic tails Y$_1$, Y$_2$ can attached through reaction of molecules having halogen leaving groups with the bis (imidazole). In FIGS. 4$a$ and 4$b$, the halogen leaving group is shown as bromine. Long tails with polymerizable groups at one end and halogen leaving groups at the other end are not believed to be commercially available. However, a molecule with these qualities, 11-bromoundecyl acrylate can be synthesized. 1,3-diene tails were used by Pindzola (2003).

As used herein, a lyotropic liquid crystal system comprises a plurality of LLC mesogens and a polar solvent, wherein the LLC mesogens form an LLC phase in combination with the solvent. A mixture comprising a plurality of LLC mesogens and a polar solvent can also be referred to as an LLC mixture. In an embodiment, the invention provides amphiphiles that form a lyotropic liquid crystal phase in the presence of water or other polar solvents. In an embodiment, the solvent is water, a room temperature ionic, or a combination thereof. The solvent may also be a combination of RTILs. In different embodiments, the lyotropic liquid crystal phase is a normal or inverted bicontinuous cubic phase, a normal or inverted hexagonal phase, or a lamellar phase. In an embodiment, the LLC phase is an inverted bicontinuous cubic phase. In an embodiment, the LLC phase is an inverted hexagonal phase.

In an embodiment, the solvent is water. When the solvent is water, the amphiphile anion may be $Br^-$.

In an embodiment, the polar solvent is a room temperature ionic liquid. A variety of room temperature ionic liquids are known to the art. In an embodiment, the RTILs is imidazolium based (the primary constituent is an imidazolium salt). In an embodiment, the RTIL is a 1,3 dialkylimidazolium salt. Common imidizalium based cations include, but are not limited to emim (1-ethyl 3-methyl imidazolium), bmim (1-butyl-3 methyl imidazolium), 1-propyl 3-methyl imidazolium, and dimethyl imidazolium. Anions commonly used in RTILS include, but are not limited to, $Br^-$, $BF_4^-$, $Cl^-$, $I^-$, $CF_3SO_3^-$, $Tf_2N^-$ (and other large fluorinated anions), $PF_6^-$, $DCA^-$, $MeSO_3^-$, and $TsO^-$.

The room temperature ionic liquid and amphiphile are selected together to produce the desired phase. In an embodiment, the amphiphile anion is not a halide ion. In an embodiment, the anion of the amphiphile matches the anion of the ionic liquid. For example, [emim][$BF_4$] is a good match for the liquid crystals that have 2 $BF_4^-$ anions associated with them. In an embodiment, the RTIL anion is $BF_4^-$. As $BF_4^-$ is small and spherical, it can readily form hydrogen bonds in all directions with the protons present on imidazolium cations, which promotes aggregation of the amphiphiles (Bradley, A. E.; Hardacre, C.; Holbrey, J. D.; Johnston, S.; McMath, S. E. J.; Nieuwenhuyzen, M. Small-Angle X-ray Scattering Studies of Liquid Crystalline 1-Alkyl-3-methylimidazolium Salts. *Chem. Mater.* 2002, 14, 629).

In an embodiment, the solution used for forming the polymerized LLC monomer, also known as the "LLC polymerization mixture", comprises a plurality of polymerizable LLC monomers, an aqueous or polar organic solvent, and a polymerization initiator. A single species of polymerizable LLC monomer may be used, but a plurality of monomers is required for phase formation. The aqueous or polar solvent is selected so that the LLC monomer forms the desired phase. Suitable polar solvents include, but are not limited to water, dimethylformamide, THF, and room-temperature ionic liquids. The polymerization initiator can be photolytically or thermally activated. The mixture is thoroughly combined. In an embodiment, mixing may be performed through a combination of hand mixing and centrifuging.

In an embodiment, the LLC polymerization mixture does not further comprise a hydrophobic polymer as described by Lu et al. (Lu, X.; Nguyen, V.; Zhou, M.; Zeng, X.; Jin, J.; Elliott, B. J.; Gin, D. L. *Adv. Mater.* 2006, 18, 3296) and U.S. Pat. No. 7,090,788.

The LLC polymerization mixture may further comprise an optional cross-linking agent. The cross-linking agent is not required if the monomer can cross-link without a cross-linking agent. In an embodiment, the cross-linking agent is not a polymer. Typically, the cross-linking agent or curing agent is a small molecule or monomeric cross linker such as divinyl benzene (DVB). Cross-linking agents are known to those skilled in the art. The amount of cross-linking agent is small enough to allow formation of the desired LLC phase. The cross-linker will typically be hydrophobic, in order to dissolve in and help to cross-link the hydrophobic tail regions of the LLC phase. For water filtration applications, it is believed that the incorporation of additional hydrophobic components into the LLC mixture should be limited to prevent the overall polymeric composition from being too hydrophobic for good water filtration. In an embodiment, the maximum amount of cross-linking agent is 10 wt % to 15 wt %. In an embodiment, when the cross-linking agent is hydrophobic its size is kept small enough so that reduction of the overall density or surface coverage of the polar solvent (e.g. water) nanopores is limited.

The LLC mixture may further comprise an organic solvent for the LLC surfactant. In an embodiment, the organic solvent is used for formulation or delivery of the LLC surfactant. The solvent may be any low boiling point solvent that dissolves the surfactant. A mixture of one or more solvents may also be used. Useful solvents include, but are not limited to, methanol and diethyl ether. In one embodiment, the monomer is dissolved in the organic solvent, and then the water and the optional cross-linking agent are added. In an embodiment when the cross-linked film is formed on a polymeric support, the organic solvent used in the solution and the support are selected to be compatible so that the support is substantially resistant to swelling and degradation by the organic solvent. Swelling and/or degradation of the support by the solvent can lead to changes in the pore structure of the support.

The composition of the LLC mixture or LLC polymerization mixture may be selected to obtain the desired phase based on the phase diagram for the LLC surfactant. For example, at atmospheric pressure the LLC phases present in the system may be determined as a function of temperature and percentage of amphiphile (LLC surfactant) in the system (e.g. Pindzola, 2003). The percentage of LLC surfactant in the mixture and the temperature can then be selected together to obtain the desired phase. When the phase of LLC mixture is sensitive to the water content, steps can be taken to minimize evaporative water loss during subsequent processing. In an embodiment, the concentration of the LLC surfactant or monomer is between 10% and 100%.

In an embodiment, the LLC mixture or polymerization mixture is allowed to assemble into the desired phase. The mixture may be allowed to rest at room temperature or at any suitable temperature dictated by the phase diagram. Analysis of the LLC phases can be performed by several methods known to those skilled in the art including polarized light microscopy (PLM) and x-ray diffraction (XRD). Q phases are optically isotropic (have a black optical texture) when viewed with the PLM. XRD of Q phases exhibit symmetry-allowed d spacings that ideally proceed in the ratio $1:1/\sqrt{2}:1/\sqrt{3}:1/\sqrt{4}:1/\sqrt{5}: 1/\sqrt{6}:1/\sqrt{8}:1/\sqrt{9}:1/\sqrt{10}: \ldots$ corresponding to the $d_{100}$, $d_{110}$, $d_{111}$, $d_{200}$, $d_{210}$, $d_{211}$, $d_{220}$, $d_{221}$(or $d_{300}$), $d_{310}$, . . . diffraction planes. The presence of Q phases with P or/symmetry in polydomain small molecule amphiphile and phase separated block copolymer systems has generally been identified on the basis of a black optical texture and a powder XRD profile in which the $1/\sqrt{6}:1/\sqrt{8}$: d spacings (i.e. the $d_{211}$ and $d_{220}$ reflections) are at least present (Pindzola, 2003). The higher order XRD reflections can be used to distinguish between the different 3-D cubic phase architectures, since systematic XRD absences in the XRD peaks result as the cubic cells becomes more complex. However, the higher order reflections may not be observed when the phases do not possess a great deal of long range order. In an embodiment, the LLC mixture has a fluid gel-like consistency before cross-linking or polymerization. XRD analysis of H phases shows d spacings that ideally proceed in the ratio $1:1/\sqrt{3}:1/\sqrt{4}:1/\sqrt{7}:1/\sqrt{9}$, while analysis of L phases shows d spacings that ideally proceed in the ratio $1:\frac{1}{2}:\frac{1}{3}:\frac{1}{4}:\frac{1}{5}\ldots$ The LLC monomers may be cross-linked to form the LLC polymer composition. As used herein, a "LLC polymer composition" comprises polymerized lyotropic liquid crystal (LLC) monomers in an ordered assembly. The LLC polymer composition may also comprise an initiator and/or a crosslinking agent. The invention also provides polymer membranes comprising cross-linked lyotropic liquid crystal (LLC) polymers formed from the LLC monomers of the invention. The membranes may formed as a film between two plates (the plates may be transparent if cross-linking is achieved through photopolymerization), or may be formed on or within a porous support. The support may be of any suitable material known to those skilled in the art including polymers, metals, and ceramics. In an embodiment, the support is a porous polymeric material. In an embodiment, the porous support is polyethylene (including high molecular weight and ultra high molecular weight polyethylene), polyacrylonitrile (PAN), polyacrylonitrile-co-polyacrylate, polyacrylonitrile-co-methacrylate, polysulfone (Psf), Nylon 6, 6, poly(vinylidene difluoride) or polycarbonate.

In an embodiment, the polymer membrane is formed on a support. Methods for forming composite membranes comprising LLC polymer porous membranes attached to a porous support are described in PCT/US2003/031429 and U.S. Patent Application Publication US 2006-0096922 to Gin et al, hereby incorporated by reference. In an embodiment, the solution for applying the lyotropic LLC monomer to the support comprises a plurality of LLC monomers, an organic solvent, water or another polar solvent, a polymerization initiator, and an optional cross-linking agent. The solvent may be any low boiling point solvent that dissolves the monomer. Application of the solution to the support can be achieved by any solution based process known to the art, including painting, rolling, spraying and inkjet printing of the solution onto the support. The solution is applied to form a coating on at least a portion of the surface of the support. The solvent may be evaporated from the film by allowing the solvent to evaporate at ambient temperature. Other temperatures and controlled atmospheres as known by those skilled in the art can be used to evaporate the solvent from the film.

In another embodiment, the polymer membrane is formed within a support. Heat and/or pressure may be used to impregnate the support with the LLC monomer. Methods for forming composite LLC membranes within a support are described in U.S. Provisional Application Ser. No. 60/938,126 to Gin et al. which is hereby incorporated by reference.

The invention also provides a method for making a cross-linked lyotropic liquid crystal polymer, the method comprising the steps of:
 a. preparing a mixture comprising a plurality of polymerizable LLC surfactants of the invention, a polymerization initiator, and a solvent selected from the group consisting of water, imidazalium based room temperature ionic liquids, and mixtures thereof; and
 b. cross-linking at least some of the polymerizable surfactants.

Polymerization of the polymerizable LLC monomer tails is performed by a chemical reaction, such as a free radical polymerization reaction. The polymerization may be initiated by irradiation with light of appropriate wavelength (i.e., photoinitiated), by introduction of a chemical reagent or catalyst and/or by thermal initiation. The composition of step (a) may further contain chemical reagents for initiation of polymerization and/or chain elongation agents and/or crosslinking reagents for the polymerization and/or crosslinking of the LLC monomer tails. Cross-linking may occur at ambient temperature (or at the required temperature to maintain the desired LLC phase). Other temperatures as known by those skilled in the art may be used during the cross-linking process. The degree of cross-linking can be assessed with infrared (IR) spectroscopy. In different embodiments, the degree of polymerization is greater than 90% or greater than 95%.

In an embodiment, the LLC monomers can be polymerized into a cross-linked network with substantial retention of the original LC phase microstructure. The LLC phase structure may be a polydomain structure, and therefore may display short-range rather than long-range order. As used herein, "nanometer scale dimension" refers to pore dimensions between about 0.5 and about 5 nm. LLC monomers useful for the present invention can form solvent nanopores having a diameter between about 0.5 and about 5 nm. As used herein, a "monodisperse" pore size has a variation in pore size from one pore to another of less than ca. 15% (specifically an ideally narrow Poisson distribution). For pores manifold systems formed by some LLC phases (e.g. bicontinuous cubic phases), the pore size of a given pore may vary along the pore channel. For pores whose dimensions vary along the pore channel, a comparison of pore sizes is made at equivalent positions along the channel. In an embodiment, the pore size is monodisperse when measured in this way.

In an embodiment, the pore structure after polymerization is substantially determined or controlled by the phase which is formed by the monomers. In this case the pore structure may be said to be based on the LLC structure. The pore structure after polymerization need not be identical to that of the LLC phase. In some LLC phases, contraction of the structure is observed on heavy cross-linking of the polymer into a network. Expansion of $Q_I$ unit cells has been observed for some LLC monomers (Pindzola et al., 2003). Some disordering of the phases may also be observed upon cross-linking, as evidenced by a loss in X-ray diffraction (XRD) peak intensity (Pindzola, 2003). In an embodiment, the pore structure of the polymerized network retains at least part of the bicontinuous cubic phase structure and comprises interconnected, ordered 3-D nanopores. Retention of the bicontinuous cubic phase structure can be confirmed through observation of XRD peaks characteristic of the structure. In other embodiments, the pore structure of the polymerized network retains at least part of the hexagonal or lamellar phase structure present in the lyotropic liquid crystal assembly.

The pore size of the nanoporous LLC assemblies can be tuned via modification of the parent LC monomer. (Resel, R.; Leising, G.; Markart, P.; Kreichbaum, M.; Smith, R.; Gin, D. "Structural Properties of Polymerised Lyotropic Liquid Crystal Phases of 3,4,5-Tris(ω-acryloxyalkoxy)benzoate Salts," *Macromol. Chem. Phys.* 2000, 201 (11), 1128). It is believed that the pore size for bicontinuous cubic phases can extend up to 5 nm. It is believed that the pore size for hexagonal phases can have a diameter between about 0.5 and about 5 nm. Pore size and pore architecture may also be tuned by changing temperature, pressure, and mixture composition, since LLC phase behavior is known to depend on all three parameters When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, starting materials, and synthetic methods, other than those specifically exemplified can be employed in the practice of the invention without resort to undue experimentation. All art-known functional equivalents, of any such methods, device elements, starting materials, and synthetic methods, are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The preceding definitions are provided to clarify their specific use in the context of the invention. All references cited herein are hereby incorporated by reference to the extent not inconsistent with the disclosure herein.

EXAMPLES

Example 1

Synthesis of 1,1'-(1,8-octanediyl)bis-imidazole

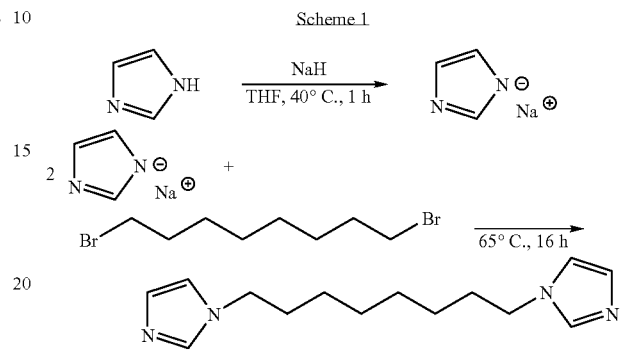

Sodium hydride (11.0 g of 60 wt % dispersion in mineral oil, 276 mmol) was added to a 500-mL, 3-neck round bottom flask equipped with stir bar and reflux condenser under argon purge. Anhydrous tetrahydrofuran (300 mL) was vacuum-transferred into the reaction vessel. Imidazole (15.0 g, 221 mmol) was added to the stirred slurry. The reaction was heated to 40° C. and held there until $H_2$ gas evolution had visibly ceased. After this time, 1,8-dibromooctane (20.4 mL, 111 mmol) was injected into the reaction mixture and the reaction heated at reflux (65° C.) under argon overnight. The reaction was allowed to cool to room temperature and the solids were filtered and washed with tetrahydrofuran. The product solution was concentrated by rotary evaporation and then dissolved in methanol (100 mL). Addition of methanol caused residual mineral oil to separate from the product. The methanol solution was washed with hexanes (3×100 mL), and concentrated by rotary evaporation. The product was dried under vacuum overnight to yield an off-white waxy solid. Yield: 21.5 g (85%).

$^1$H NMR (400 MHz, CDCl$_3$): δ=7.471, 7.270, 7.063, 6.901, 3.940-3.905, 1.776-1.741, 1.286-1.257

Example 2

Synthesis of 1,1'-(1,8-octanediyl)bis[3-[11-hydroxyundecyl]]-imidazolium ditetrafluoroborate

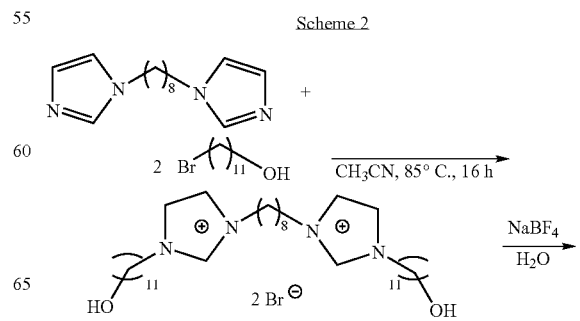

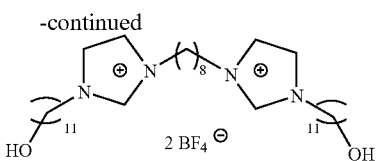

1,1'-(1,8-hexanediyl)bis-imidazole (5.0 g, 20 mmol) and 11-bromo-1-undecanol (10.3 g, 41 mmol) were added to a 250-mL round bottom flask with stir bar. Acetonitrile (125 mL) was added, a reflux condenser was attached and the reaction was stirred at 85° C. overnight. The reaction was stopped and solvent removed by rotary evaporation. Diethyl ether was added to the crude product and the mixture was stirred. Solids were filtered and collected. The dibromide salt was then dissolved in a 250-mL round bottom flask with warm deionized water (125 mL). Sodium tetrafluoroborate (18.0 g, 164 mmol) was added to the solution, which caused a precipitate to form immediately. The flask was placed in a refrigerator overnight. The waxy solids were filtered and washed with deionized water then dried under vacuum overnight. Yield: 11.5 g (74%).

$^1$H NMR (400 MHz, DMSO-$d_6$): δ=9.692, 7.798, 7.689-7.681, 7.606-7.597, 4.219-4.176, 4.035-4.010, 3.424-3.379, 3.175, 2.509-2.491, 1.866-1.810, 1.433-1.399, 1.381-1.189

Example 3

Synthesis of 1,1'-(1,8-octanediyl)bis[3-[11-acryloyloxyundecyl]]-imidazolium ditetrafluoroborate

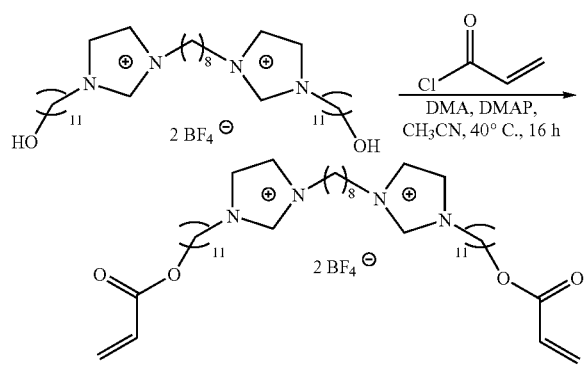

1,1'-(1,8-octanediyl)bis[3-[11-hydroxyundecyl]]-imidazolium ditetrafluoroborate (10.0 g, 13.1 mmol) was added to a 250-mL air- and water-free Schlenk flask. Anhydrous acetonitrile (100 mL) was added, followed by N,N'-dimethylaniline (8.8 mL, 69 mmol) and 4-dimethylaminopyridine (0.16 g, 1.3 mmol). After addition of acryloyl chloride (2.57 mL, 31.4 mmol) the reaction was heated to 40° C. and stirred under argon overnight. The reaction was cooled to room temperature then poured into 500 mL of 1.2 M hydrochloric acid. The product was extracted with ethyl acetate (3×250 mL) and dried over anhydrous magnesium sulfate. The solids were filtered and the solvents removed by rotary evaporation. The remaining viscous oil was washed with diethyl ether and dried under vacuum lines. The oil became a waxy solid after standing 24 hours at room temperature. Yield=8.5 g (75%).

$^1$H NMR (400 MHz, CDCl$_3$): δ=9.145, 7.831-7.812, 7.555-7.518, 7.313-7.289, 6.433-6.396, 6.168-6.113, 5.854-5.830, 4.269-4.149, 3.508-3.480, 3.212, 1.925-1.898, 1.708-1.665, 1.370-1.217

Example 4

Figure 5:
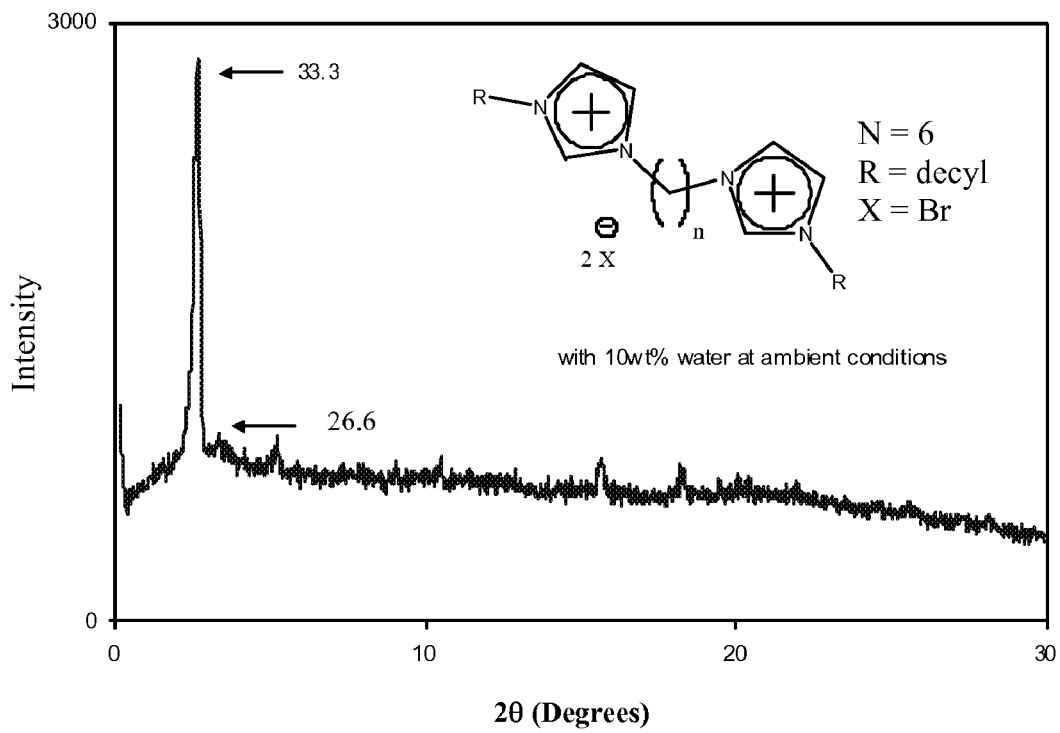
FIG. 5: XRD profile of the Q LLC phase of a non-polymerizable example of a gemini imidazolium surfactant formed with 10 wt % water as the polar solvent.

Formation of Q phases for Non-polymerizable Imidazolium-Based Gemini Amphiphiles in Water and a RTIL FIG. 5 shows a powder X-ray diffraction (XRD) spectrum of the room temperature Q LLC phase formed in a mixture of 10 wt % water and an amphiphile having a two Br— anions and a pair of imidazolium-based cations, each having a 10 carbon linear alkyl tail and joined with an 8 carbon linear alkylene spacer.

Figure 6:
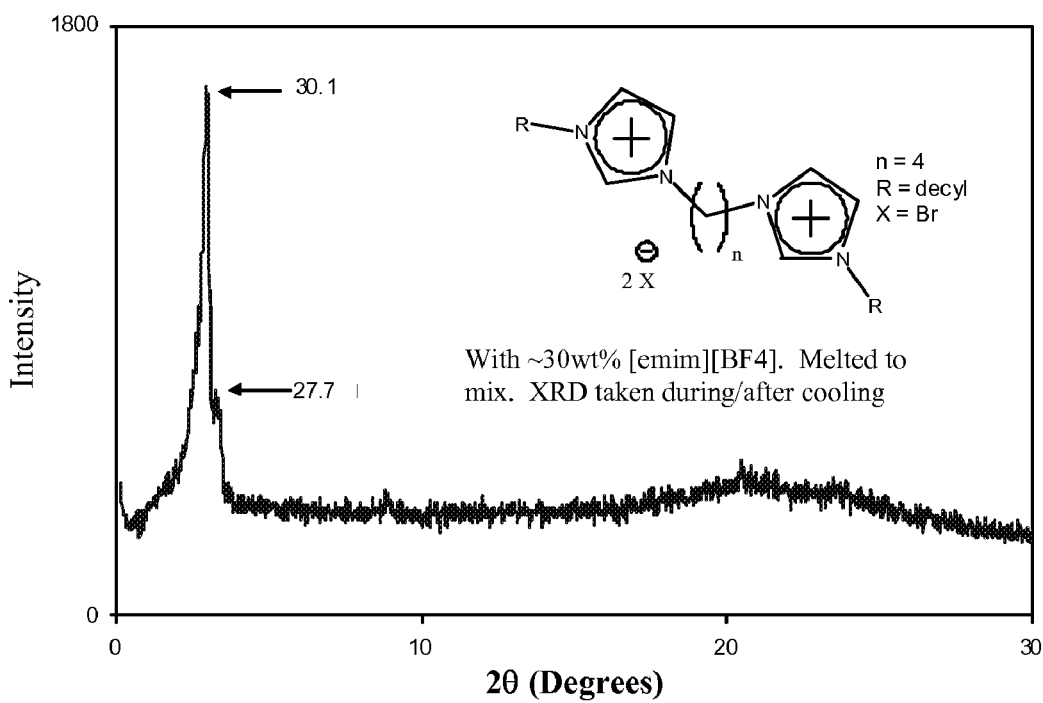
FIG. 6: XRD profile of the Q LLC phase of a non-polymerizable example of a gemini imidazolium surfactant formed with 30 wt % RTIL ([emim][$BF_4$]) as the polar solvent.

FIG. 6 shows an powder X-ray diffraction (XRD) spectra of the room temperature Q LLC formed in a mixture of approximately 30 wt % [emim]BF$_4^-$] and an amphiphile having a two Br— anions and a pair of imidazolium-based cations, each having a 10 carbon linear alkyl tail and joined with an 4 carbon linear alkylene spacer.

The most intense XRD peaks in the spectra have the distinctive 1/√6:1/√8 d-spacing ratio characteristic of a Q phase with either the Ia3d or Pn3m space groups (Fontell 1990; Mariani, P.; Luzzati, V.; Delacroix, H. *J. Mol. Biol.* 1988, 204,165) The identities of the ordered Q phases formed by these surfactants with water and RTIL are further confirmed by the presence of black optical textures for the cubic LC phases under a polarized microscope.(Tiddy 1980; Seddon 1990), Example 5

Formation of a Ordered Phase for a Polymerizable Gemini Surfactant

Figure 7:
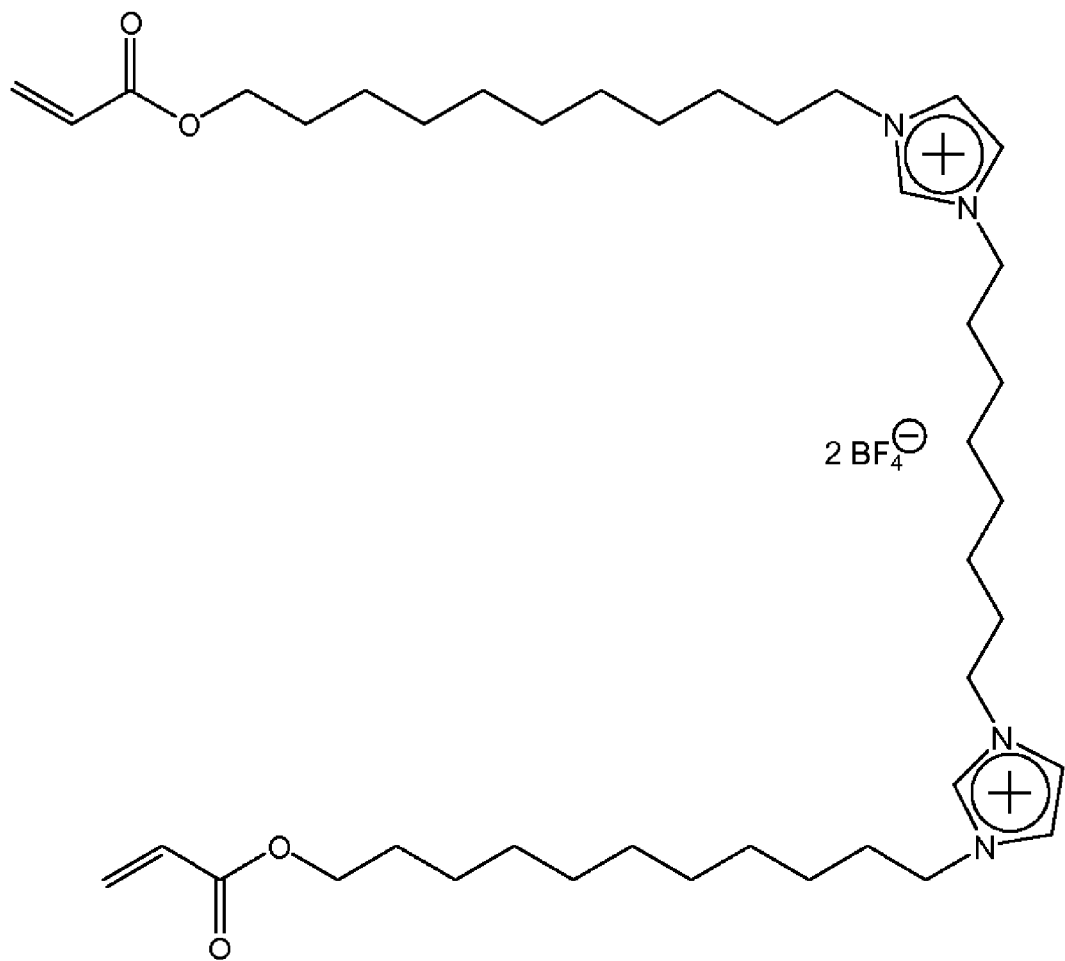
FIG. 7: Photocrosslinkable gemini imidazolium surfactant having an alkylene spacer.
Figure 8:
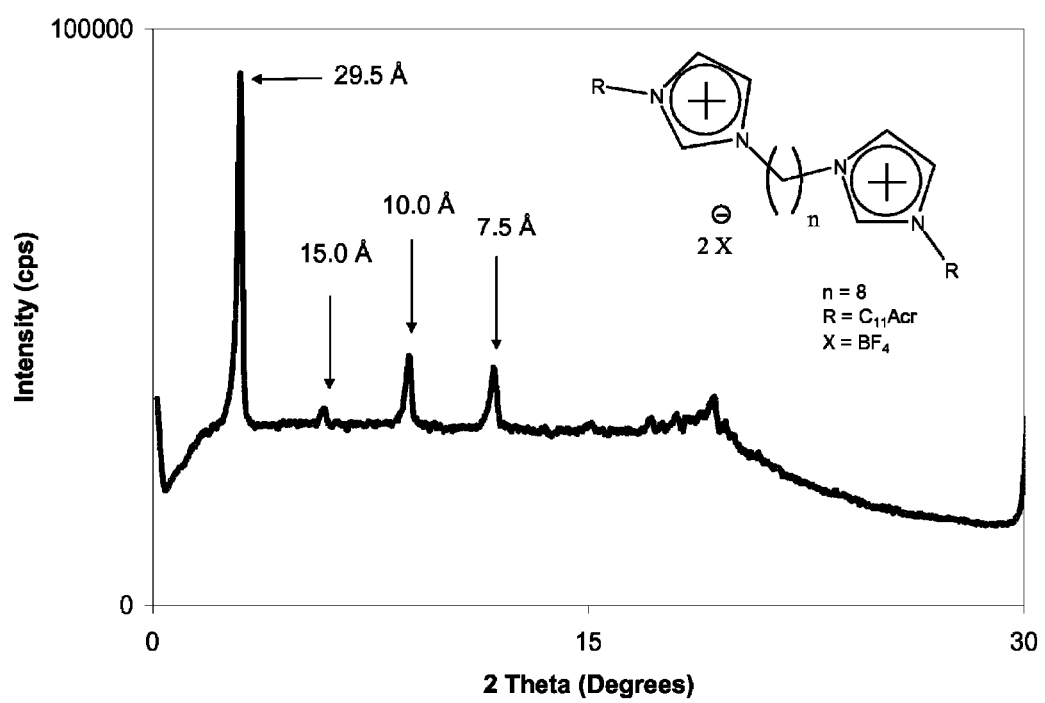
FIG. 8: XRD profile of the phase of a polymerizable example of a gemini imidazolium surfactant as a neat material exposed to ambient conditions. The peaks are in the ratio 1:½:⅓:¼ . . . .
Figure 9:
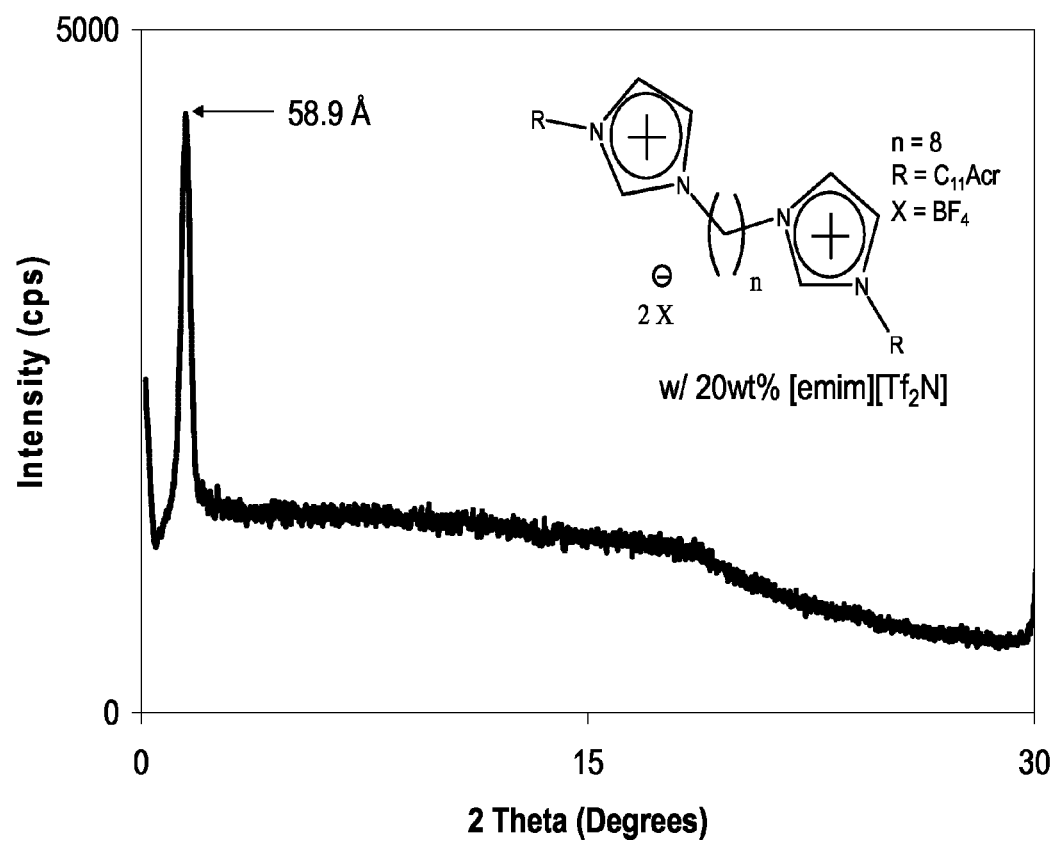
FIG. 9: XRD profile of a Q LLC phase of a polymerizable example of a gemini imidazolium surfactant when mixed with [emim][$TF_2N$], a common RTIL.

FIG. 7 shows a crosslinkable Gemini surfactant having a pair of BF$_4^-$ anions, a pair of C$_{11}$acrylate tails, and a linear alkylene spacer with 8 carbon atoms. Using the crosslinkable gemini surfactant shown in FIG. 7, ordered freestanding films have been successfully fabricated via photopolymerization. The phase behaviors exhibited by this system in a neat form and when mixed with a common RTIL (20 wt % [emin][Tf$_2$N] are shown in FIGS. 8 and 9, respectively. The XRD phase peaks in FIG. 8 are in the ratio: 1:½:⅓:¼... (indicating the lamellar phase). Similar peak ratios were observed when the monomer was mixed with small amounts of [emin][BF4]. To form the polymerized film, 20 weight percent of the monomer of FIG. 7 was mixed with 20 wt % [emim][TF$_2$N] and 1 wt % photoinitiator. The mixture was squeezed between two quartz plates and exposed to 365 nm light for between 15 and 30 minutes.

Example 6

Figure 10:
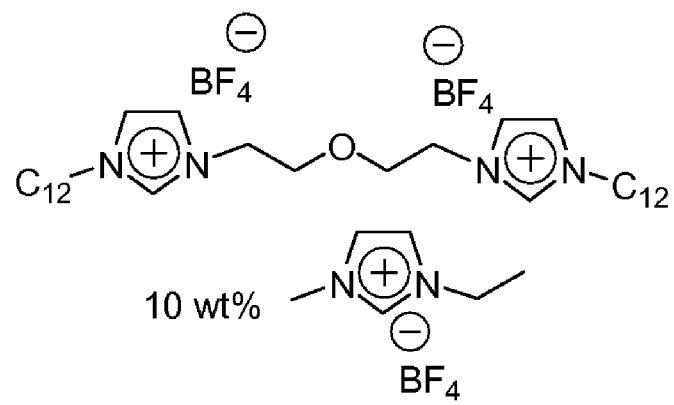
FIG. 10: Photocrosslinkable gemini imidazolium surfactant having an ether containing spacer.

Formation of an H-phase Structure with a Polymerizable Gemini Surfactant in a RTIL Mixing of the amphiphile shown in FIG. 10 with 10 wt % [C$_2$mim][BF$_4$], resulted in the formation of a hexagonal phase, as confirmed visually by a fan-like optical texture on a PLM image. The amphiphile shown in FIG. 10 can be synthesized similarly to amphiphiles with alkylene spacer, except that a spacer precursor is an oligo(ethylene glycol) chain capped by two leaving groups (e.g. CI, Br, I, OTs ("Tosylate"), etc. . . . )

The use of oligo(ethylene glycol) spacers (as in the amphiphile in FIG. 10) appears to have significant effects on LLC phase stability, as well as on the types of LLC phases that can be formed. Since oxygen-containing functional groups tend to interact with and are compatible with imidazolium salts (Yoshio, M.; Mukai, T.; Kanie, K.; Yoshizawa, M.; Ohno, H.; Kato, T. *Adv. Mater.* 2002, 14, 351; Jin, C.-M.; Ye, C.; Phillips, B. S.; Zabinski, J. S.; Liu, X.; Liu, W.; Shreeve, J. M. *J. Mater. Chem.* 2006, 16, 1529; Hu, X.; Tang, J.; Blasig, A.; Shen, Y.; Radosz, M. *J. Membr. Sci.* 2006, 281, 130) the presence of oligo(ethylene glycol) linkages appears to promote different types of aggregation by the surfactants. The oligo(ethylene glycol)-based spacers are miscible with the imidazolium cations of the LLC mesogen as well as those in the RTIL solvent, which promotes organization at the headgroups. The use of a spacer with oligo(ethylene glycol) linkages and the presence of $BF_4^-$ anions appears to promote aggregation of the headgroups with each other and around an RTIL solvent.

In addition, the incorporation of a $BF_4^-$ anion is believed to be beneficial. LLCs with $BF_4^-$ anions can be mixed with the RTIL solvents similar to $[C_2mim][BF_4]$. Large anions, such as bis(trifluoromethane)sulfonimide, $(Tf_2N^-)$, have not produced stable LLC structures in these gemini surfactants due to their asymmetric shapes and very weak basicities, which limit their hydrogen-bonding ability Without wishing to be bound by any particular theory it is believed that interactions of ethers with cations and anions with cations, coupled with the immiscibility of oligo(ethylene glycol) units with alkyl chains, forces segregation on the nanometer scale. Together with packing preferences due to the overall shape of the molecules, formation of a columnar H phase is believed to be promoted.

Example 7

Figure 11:
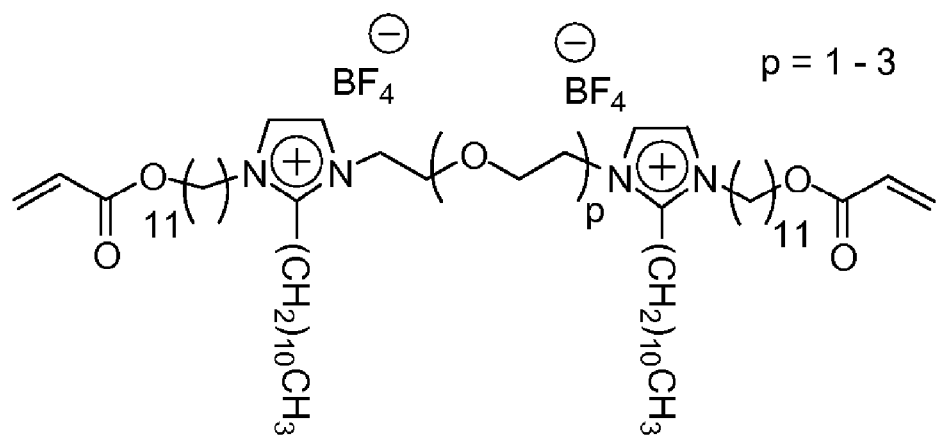
FIG. 11: Photocrosslinkable gemini imidazolium surfactant having an ether containing spacer and additional hydrophobic tails.

Formation of a Q-phase Structure with a Polymerizable Gemini Surfactant in a RTIL The derivative shown in FIG. 11, with p=1, has several properties characteristic of a Q-phase material: viscous physical texture and optical transparency (resulting in an entirely black PLM image lacking any optical texture)(Lu, X.; Nguyen, V.; Zhou, M.; Zeng, X.; Jin, J.; Elliott, B. J.; Gin, D. L. *Adv. Mater.* 2006, 18, 329).

Figure 12:
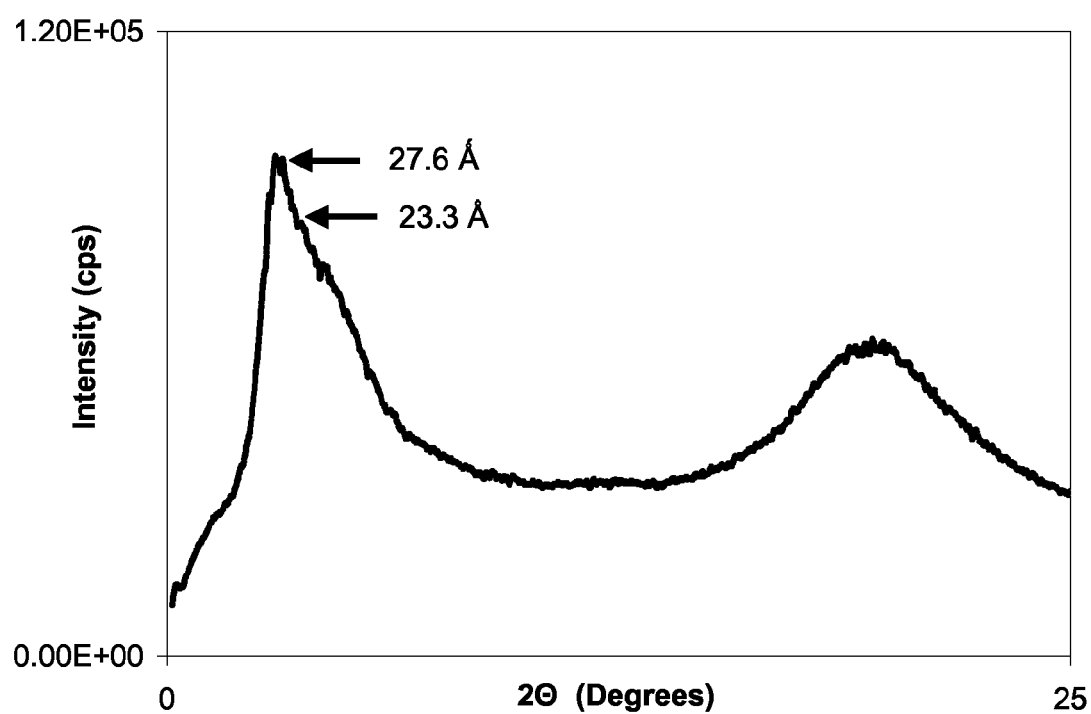
FIG. 12: XRD profile of a polymer film formed from the gemini surfactant (p=1) detailed in FIG. 11.

FIG. 12 shows an XRD profile obtained for the cross-linked film of the LLC of FIG. 11. The monomers were mixed with approximately 5 wt % [emim][$BF_4$] and 1% or less photoinitiator (2-hydroxy-2-methyl-propiophenone, Aldrich) and then polymerized. The ratio of the d-spacings for the first two peaks observed is very close to $1/\sqrt{6}:1/\sqrt{8}$, which is indicative of the presence of a Q-phase (Pindzola 2003, Lu 2006; Fontell 1990; Mariani 1998). The second peak may have been obscured as a consequence of polymerization, as it is visible only as a shoulder to the first.

We claim:
1. A polymerizable surfactant composition having the general formula:

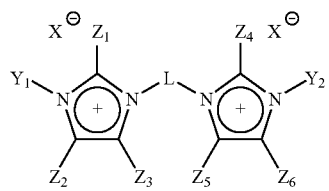

wherein X is an anion;
Y$_1$ and Y$_2$ each are a hydrophobic tail group consisting of a linear alkylene group attached to a polymerizable group P, with the tail group as a whole having at least 10 carbon atoms;

$Z_1, Z_2, Z_3, Z_4, Z_5$ and $Z_6$ each are hydrogen or a hydrophobic tail group comprising from 1 to 12 carbon atoms; and
L is a spacer group which comprises an alkylene group having from 1 to 12 carbon atoms, comprises 1 to 6 ether groups or is $-(CH_2CH_2-(O-CH_2-CH_2)_p-$, where p is 1 to 3.

2. The surfactant composition of claim 1 wherein L is $-(CH_2)_n$, n is 1 to 10.

3. The surfactant composition of claim 1, wherein L is $-(CH_2CH_2-(O-CH_2-CH_2)_p-$, p is 1 to 3.

4. The surfactant composition of claim 1, wherein the polymerizable group P is an acrylate, methacrylate or diene group.

5. The surfactant composition of claim 4, wherein the polymerizable group P is an acrylate group.

6. A lyotropic liquid crystal system comprising a surfactant having the composition given by

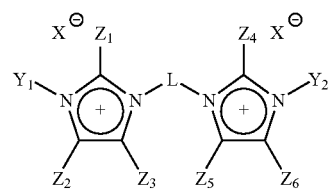

Wherein X is an anion;
Y$_1$ and Y$_2$ each are a hydrophobic tail group comprising at least 10 carbon atoms and optionally comprising a polymerizable group;
$Z_1, Z_2, Z_3, Z_4, Z_5$ and $Z_6$ each are hydrogen or a hydrophobic tail group comprising from 1 to 12 carbon atoms; and
L is a spacer group which comprises an alkylene group having from 1 to 12 carbon atoms, comprises 1 to 6 ether groups, or is $-(CH_2CH_2-(O-CH_2-CH_2)_p-$, where p is 1 to 3; and
a polar solvent,
wherein the concentration of the surfactant is between 10 wt % and 100 wt % and the surfactant forms a lyotropic liquid crystal phase in combination with the solvent.

7. The lyotropic liquid crystal system of claim 6, wherein the surfactant forms a bicontinuous cubic phase in combination with the solvent.

8. The lyotropic liquid crystal system of claim 6, wherein the surfactant forms a hexagonal phase in combination with the solvent.

9. The lyotropic liquid crystal system of claim 6, wherein the polar solvent is selected from the group consisting of water, imidazolium based room temperature ionic liquids, and mixtures thereof.

10. The lyotropic liquid crystal system of claim 6, wherein L is $-(CH_2)_n$, n is 1 to 10.

11. The lyotropic liquid crystal system of claim 6, wherein L is $-CH_2CH_2-(O-CH_2-CH_2)_p-$, p is 1 to 3.

12. The lyotropic liquid crystal system of claim 6, wherein Y$_1$ and Y$_2$ comprise a polymerizable group.

13. A cross-linked lyotropic liquid crystal (LLC) polymer comprising polymerizable surfactants which have been crosslinked, wherein the cross-linked polymerizable surfactants form a LLC phase and the polymerizable surfactants have the general formula:

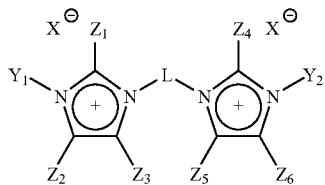

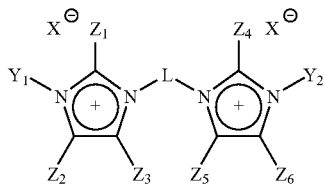

wherein X is an anion;

$Y_1$ and $Y_2$ each are a hydrophobic tail group comprising a polymerizable group P, and at least 10 carbon atoms;

$Z_1, Z_2, Z_3, Z_4, Z_5$ and $Z_6$ each are hydrogen or a hydrophobic tail group comprising from 1 to 12 carbon atoms; and L is a spacer group which comprises an alkylene group having from 1 to 12 carbon atoms, comprises 1 to 6 ether groups or is $-(CH_2CH_2-(O-CH_2-CH_2)_p-$, where p is 1 to 3.

14. The cross-linked LLC polymer of claim 13, wherein the cross-linked LLC polymer forms a bicontinuous cubic phase.

15. The cross-linked LLC polymer of claim 14, wherein the cross-linked LLC polymer forms an inverted bicontinuous cubic phase.

16. The cross-linked LLC polymer of claim 13, wherein the cross-linked LLC polymer forms a hexagonal phase.

17. The cross-linked LLC polymer of claim 13, wherein the surfactant composition is such that L is $-CH_2CH_2-(O-CH_2-CH_2)_p-$, p is 1 to 3.

18. A method of making a cross-linked lyotropic liquid crystal (LLC) polymer, the method comprising the steps of:
  a. preparing an LLC polymerization mixture comprising a plurality of a polymerizable surfactant, a polymerization initiator and a polar solvent selected from the group consisting of water, imidazolium based room temperature ionic liquids, and mixtures thereof, wherein the surfactant forms a lyotropic liquid crystal phase in combination with the solvent and the polymerizable surfactants has the general formula:

wherein X is an anion;

$Y_1$ and $Y_2$ each are a hydrophobic tail group comprising a polmerizable group P, and at least 10 carbon atoms;

$Z_1, Z_2, Z_3, Z_4, Z_5$ and $Z_6$ each are hydrogen or a hydrophobic tail group comprising from 1 to 12 carbon atoms; and L is a spacer group which comprises an alkylene group having from 1 to 12 carbon atoms, comprises 1 to 6 ether groups or is $-(CH_2CH_2-(O-CH_2-CH_2)_p-$, where p is 1 to 3;

b. cross-linking at least some of the surfactants.

19. The method of claim 18, wherein the degree of cross-linking is at least 90%.

20. The method of claim 18, wherein the surfactant composition is such that L is $-CH_2CH_2-(O-CH_2-CH_2)_p-$, p is 1 to 3.

21. The method of claim 18, wherein the surfactant forms a bicontinuous cubic phase.

22. The method of claim 18, wherein the surfactant forms a hexagonal phase.

23. The surfactant composition of claim 3, wherein the polymerizable group P is an acrylate group, $Z_1$ and $Z_4$ are a hydrophobic tail group and $Z_2, Z_3, Z_5$ and $Z_6$ are hydrogen.

24. The lyotropic liquid crystal system of claim 11, wherein the polymerizable group P is an acrylate group, $Z_1$ and $Z_4$ are a hydrophobic tail group and $Z_2, Z_3, Z_5$ and $Z_6$ are hydrogen.

* * * * *